United States Patent
Lipman

Patent Number: 5,916,270
Date of Patent: *Jun. 29, 1999

[54] HIP REPLACEMENT

[75] Inventor: Joseph David Lipman, New York, N.Y.

[73] Assignee: New York Society for the Ruptured and Crippled Maintaining the Hospital for Special Surgery, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/870,186

[22] Filed: Jun. 6, 1997

[51] Int. Cl.$^6$ ................................. A61F 2/34; A61F 2/36
[52] U.S. Cl. ................................. 623/22; 623/23
[58] Field of Search ................... 623/18, 21, 22, 623/23

[56] References Cited

U.S. PATENT DOCUMENTS

| | | |
|---|---|---|
| 807,473 | 12/1905 | Kolar . |
| 3,815,157 | 6/1974 | Skorecki et al. . |
| 3,863,273 | 2/1975 | Averill . |
| 3,916,451 | 11/1975 | Buechel et al. . |
| 3,924,275 | 12/1975 | Heimke et al. . |
| 4,172,296 | 10/1979 | D'Errico ................................. 623/22 |
| 4,279,041 | 7/1981 | Buchholz . |
| 4,778,474 | 10/1988 | Homsy ................................. 623/22 |
| 4,808,186 | 2/1989 | Smith . |
| 4,846,840 | 7/1989 | Leclercq et al. . |
| 4,950,300 | 8/1990 | Langlais . |
| 4,969,910 | 11/1990 | Frey et al. ................................. 623/22 |
| 5,041,140 | 8/1991 | Teinturier ................................. 623/23 |
| 5,387,244 | 2/1995 | Breard ................................. 623/23 |
| 5,549,698 | 8/1996 | Averill et al. ................................. 623/22 |
| 5,658,345 | 8/1997 | Willi ................................. 623/22 |

FOREIGN PATENT DOCUMENTS

| | | | |
|---|---|---|---|
| 0461019 | 12/1991 | European Pat. Off. ................. 623/22 |
| 231175 | 9/1974 | Germany ................................. 623/22 |
| 2935511 | 3/1981 | Germany ................................. 623/22 |
| 1711867 | 2/1992 | U.S.S.R. ................................. 623/22 |

OTHER PUBLICATIONS

Thackray® Wroblewski, 1984 (3 pgs.).

*Primary Examiner*—Bruce E. Snow
*Attorney, Agent, or Firm*—Darby & Darby

[57] ABSTRACT

A hip replacement for reducing the likelihood of joint dislocation and including a femoral component having a head and an elongated neck and an acetabular cup formed with a socket to capture the head. The socket includes a formed annular liner defining a stop to engage the neck during extreme motion. The neck contact surface and annular liner cooperate to shift the resultant contact point radially outwardly from the head to minimize dislocation resulting from the moment acting upon the femoral component.

2 Claims, 3 Drawing Sheets

HIP REPLACEMENT

FIELD OF THE INVENTION

The invention relates to prostheses, and more particularly an acetabular cup and femoral component configured for a hip replacement system to reduce the likelihood of dislocation.

BACKGROUND OF THE INVENTION

Artificial joints provide patients having arthritic or otherwise dysfunctional skeletal features with an alternative treatment for the chronic pain and discomfort often associated with such problems. Correction of the condition generally involves surgically replacing one or more of the natural components making up the joint with an artificial equivalent.

One of the more widely implemented artificial joints serves as a substitute for hips. A typical hip replacement system generally includes a femoral prosthesis implanted in the upper end of the femur when the femoral head requires replacement. The replacement is formed with a spherically shaped head and an elongated narrow neck extending from the head and connected to a stem which can be attached to the femur. The femoral head is pivotally nested within the socket of an acetabular cup. The cup includes a hemispherical base for mounting to the pelvis, and an outwardly opening socket to receive the femoral head. The prosthesis components are implanted during a surgical procedure well known to those skilled in the art.

While the typical hip replacement system described above provides a moderate range of mobility, the acetabular cup generally has limited clearance with respect to the neck of the femoral prosthesis. As a result, attempts by the patient to forcefully move the joint beyond the designed range of motion may cause the femoral head to pop out of the cup, resulting in dislocation that ultimately may require subsequent surgery for correction.

One attempt to expand the range of movement is disclosed in U.S. Pat. No. 5,387,244. The joint includes an acetabular cup with a bevelled edge for anchoring to the pelvis and a femoral prosthesis configured with a spherical head and a neck formed in lateral offset relation away from the medial side to the longitudinal axis of the femoral prosthesis. The neck includes a formed contact surface to complementally engage the bevelled edge of the cup to define a maximum degree of flexion.

While the design above may provide a relatively moderate range of mobility, the problem of dislocation remains unresolved. Dislocation typically occurs when the neck of the femoral component contacts the acetabular liner and rotates about that contact point. For the modified hip replacement system described above, the resultant contact point defined by the beveled edge and the contact surface occurs near the head center to create a fixed fulcrum that cooperates with the bulk of the prosthesis length to generate a relatively large moment. Under some circumstances, this moment is capable of dislodging or dislocating the head out of the cup. Moreover, continuous impact between these components can cause wear debris to accumulate in the joint.

Therefore, the need exists for a hip replacement system configured to minimize the occurrence of dislocation of the femoral component and the cup. The hip replacement of the present invention satisfies these needs.

SUMMARY OF THE INVENTION

The hip replacement of the present invention provides patients the capability of carrying out everyday tasks with the reduced likelihood of component dislocation. This reduces the complications and expense arising from reassembling the joint through subsequent surgery or the like. It also reduces the accumulation of wear debris caused by impacts between the hip components. Additionally, the design of the hip replacement expands the range of flexion for the joint to correspondingly create a wider range of mobility for the patient.

To realize the advantages described above, the present invention, in one form, comprises an acetabular cup for mating to a femoral component comprising a ball-shaped head and a reduced-diameter neck, i.e. a neck having a diameter less than the diameter of the head. The component neck extends from the head and has a contact surface. The cup includes a socket adapted to pivotally retain the femoral component head. The socket is bounded peripherally by a rim which forms an engagement surface to define a stop which engages the contact surface to establish an initial contact point corresponding to a predetermined motion limit for the femoral component. As the hip joint moves beyond this motion limit, the contact point shifts radially outwardly along the surface to reduce the likelihood of dislocation.

Other features and advantages of the present invention will be apparent from the following detailed description when read in conjunction with the accompanying drawings.

DETAILED DESCRIPTION OF THE INVENTION

A human hip joint typically comprises a socket portion formed in the pelvis to rotatably capture a ball-shaped head portion projecting inwardly from the femur bone. Severe dysfunction of the joint often requires hip arthroplasty, involving a surgical substitution of the socket portion, the head portion, or both.

Figure 1:
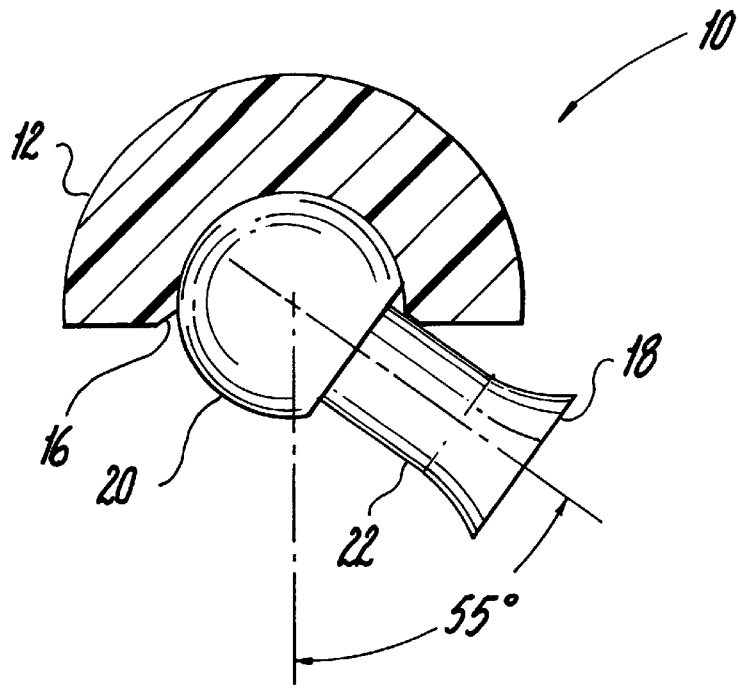
FIG. 1 is a lateral sectional view of a conventional hip replacement system.
Figure 2:
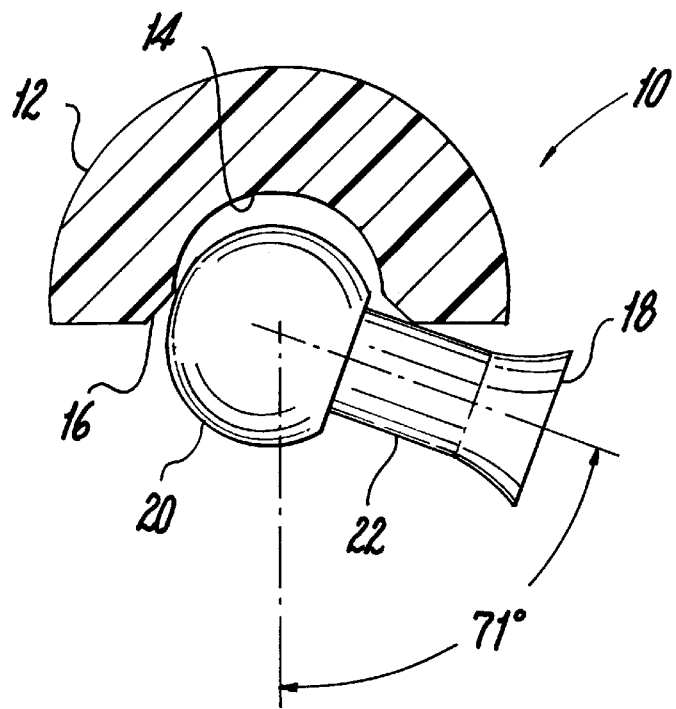
FIG. 2 is a view similar to FIG. 1 showing a maximum degree of deflection before dislocation.

Referring now to FIGS. 1 and 2, a conventional hip replacement system for substituting a human hip joint, generally designated 10, includes an acetabular cup 12 and a femoral element 18. The acetabular cup is configured with a curved (for example, hemispherical) shape and is formed with a central cavity 14 (FIG. 2) that opens radially outwardly to define a socket. The socket is bounded radially by a chamfered anterior rim 16 that extends radially outwardly to define a flat surface. During the arthroplasty procedure, the cup is typically implanted in the pelvis.

Further referring to FIGS. 1 and 2, the femoral component 18 is typically implanted into the femur bone and includes a formed mushroom shaped head 20 for rotatably nesting in the cup socket 14. Projecting outwardly from the head is a formed neck that angles radially outwardly to define a shaft 22. The neck forms an engagement surface for impinging on the surface of rim 16 during extreme movement of the joint.

Dislocation of the components comprising a conventional hip replacement system typically results from an overabundance of leverage caused by extreme movement. FIG. 1 illustrates the cup 12 and the femoral element 18 oriented with the neck initially impinging on the anterior rim, but with the head 20 still securely nested in the socket 14. Continued flexure of the joint beyond the orientation shown in FIG. 1 results in the head popping out of the socket, as shown in FIG. 2, due to the fixed leverage created at the contact point.

Figure 3:
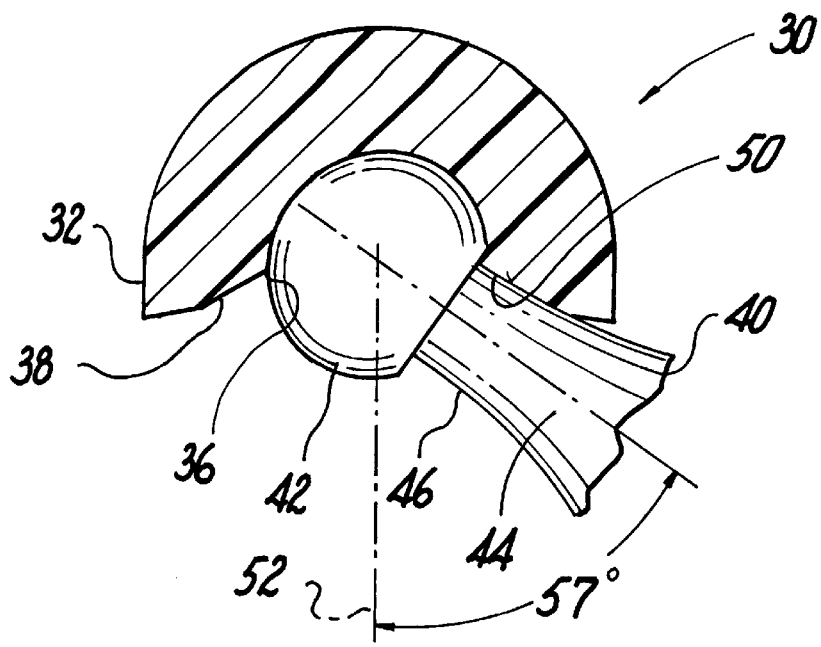
FIG. 3 is a lateral sectional view of the present invention according to a first embodiment.
Figure 4:
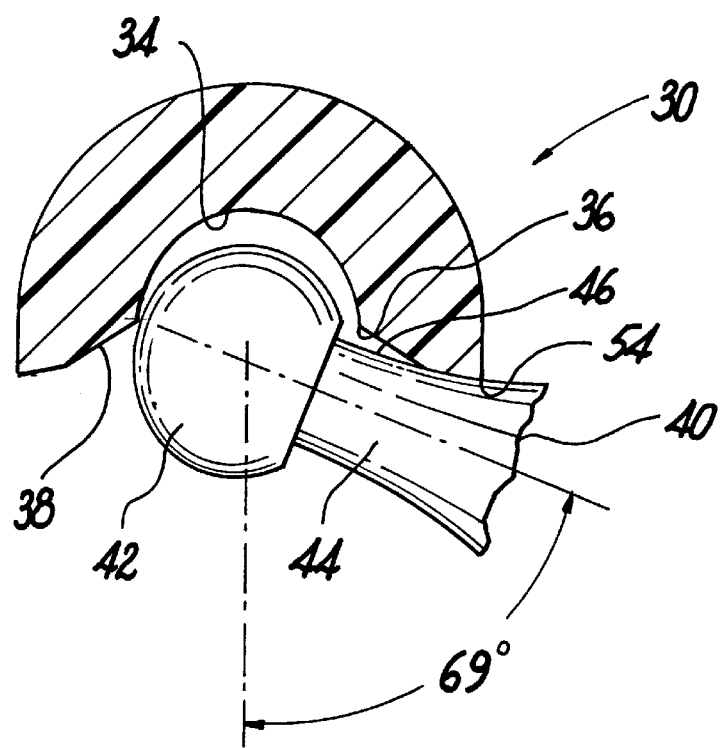
FIG. 4 is a view similar to FIG. 3.

Referring now to FIGS. 3 and 4, the hip replacement system of the present invention, according to a first embodiment, and generally designated 30, reduces the dislocation problem described above by providing an acetabular cup 32 that cooperates with a femoral component 40 to establish decreasing leverage on the femoral component during extreme movement of the joint.

With continuing reference to FIG. 3, the acetabular cup 32 may be C shaped in cross-section, with a centrally formed cavity 34 (FIG. 4) defining a hemispherical socket (for example) and bounded radially by a rim has a convex surface which 38. The rim extends radially outwardly at an angled orientation to from point 36.

The femoral component 40, which may be the same as the femoral component shown in FIGS. 1 and 2, comprises a ball-shaped head 42 and a reduced-in-diameter neck 44 extending from the head and having a formed contact surface 46. As shown in FIGS. 3–6, the opening of the socket formed by the acetabular cup is slightly larger than the diameter of the femoral head and, therefore, the socket itself does not prevent withdrawal of the head from the socket.

During an arthroplasty procedure, the acetabular cup 32 is implanted into the pelvis (not shown), while the femoral component 40 is implanted into a surgically modified femur bone (not shown). Following the surgical procedure, the joint is fully operative to allow relative rotation between the two components.

As shown in FIG. 3, operation of the hip replacement 30 will often involve movement to an orientation such that the contact surface 46 of the neck 44 abuts the rim surface 38 at an initial contact point 50 corresponding to a predetermined motion limit for the femoral component. The initial contact orientation, according to a first embodiment, comprises fifty seven degrees of deflection as compared to a socket central axis 52. Further flexing of the joint places an increased load on the femoral component resulting from leverage being exerted at the initial contact point.

However, as shown in FIG. 4, due to the unique declining angular convex configuration of the rim liner 38, as the hip joint moves beyond this motion limit, the contact point shifts radially outwardly along the rim to a peripheral contact point 54 allowing a maximum deflection of sixty nine degrees, while reducing the dislocation leverage acting on the femoral component. Additionally, by decreasing the dislocation leverage acting on the femoral component, an oppositely directed restoring moment is increased to maintain the component within the socket.

Figure 5:
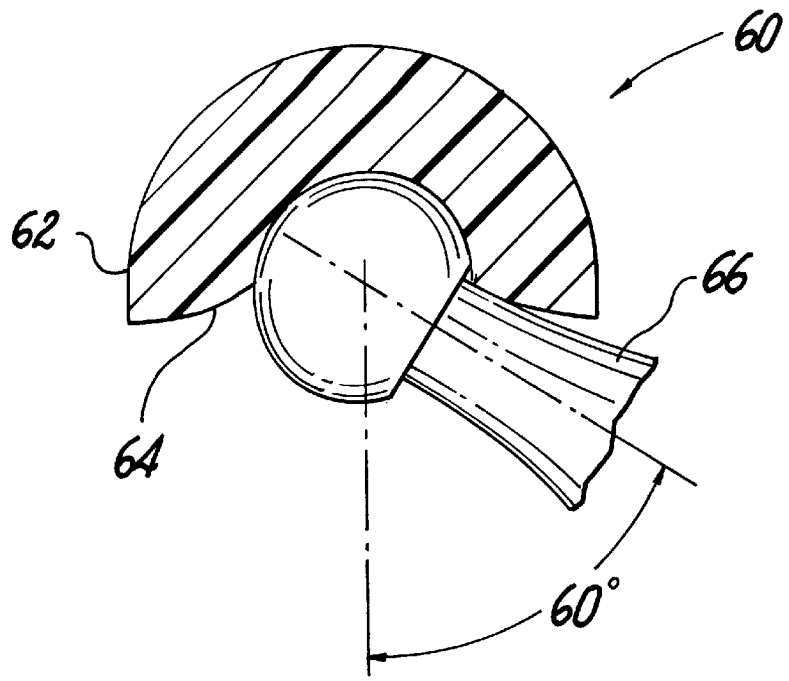
FIG. 5 is a lateral sectional view of the present invention according to a second embodiment.
Figure 6:
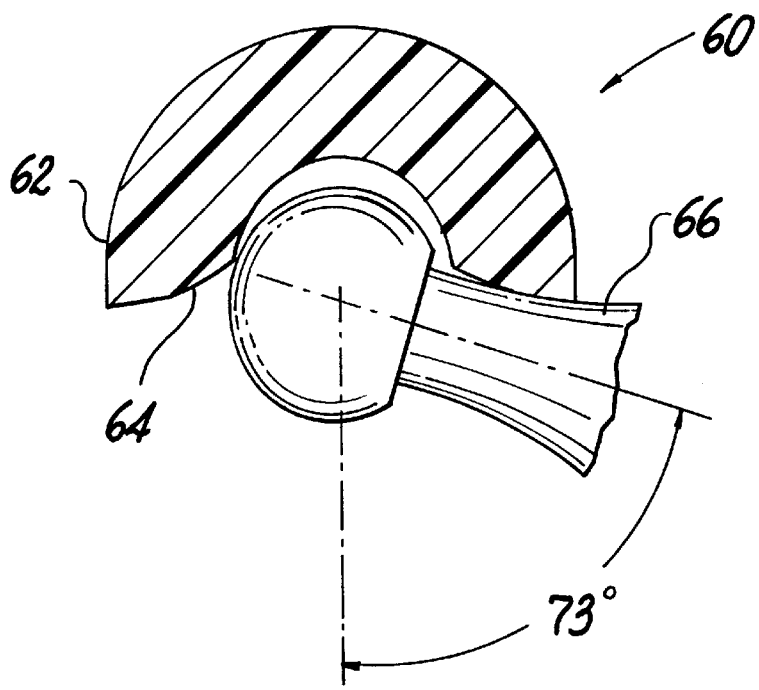
FIG. 6 is a view similar to FIG. 5.

Referring now to FIG. 5, a second embodiment of the present invention, generally designated 60, implements an acetabular cup 62 formed substantially similar to that of the first embodiment, but having a less pronounced angular decline for the convex surface 64. A femoral component 66 is also included which is formed substantially similar to that of the first embodiment.

It has been discovered that by making the angle of decline less pronounced for the surface 64 with respect to the angle implemented for the surface according to first embodiment of the present invention, during operation, the contact point shifts radially outwardly, unexpected allowing an unexpected advantage in relative mobility from sixty nine degrees to seventy three degrees. On the other hand, the steeper angle of decline of FIGS. 3 and 4 will produce a higher restoring moment during subluxation.

In the illustrated embodiments, the rim surface 38 is convex and the contact surface 46 of neck 44 concave. Other shapes for these surfaces are also contemplated. For example, the surface 38 may be curved and the surface 46 straight, i.e. not curved in cross section, or surface 46 may be curved and surface 38 straight. Possibly, surface 38 may be concave and surface 46 convex. The invention contemplates any surface configurations which enable the contact point between the neck and the rim to move outwardly or toward the periphery of the rim as motion of the femoral component increases.

It is also envisioned that the present invention may be individually packaged and sold as a kit of unassembled components to reduce any unnecessary costs associated with purchasing an entire system, should only the need for one component of the system arise.

Those skilled in the art will appreciate the many benefits and advantages realized by the present invention. Of paramount importance is the shifting contact point feature that reduces leverage acting upon the femoral component to pop it from the cup socket. As a direct result, severe dislocations that may degrade the performance of the joint are substantially reduced. Moreover, by greatly reducing the number of dislocations between the hip joint components, subsequent costly surgical corrections are dramatically minimized.

While the invention has been particularly shown and described with reference to the preferred embodiments thereof, it will be understood by those skilled in the art that various changes in form and detail may be made therein without departing from the spirit and scope of the invention.

What is claimed is:

1. A replacement hip system including:
   a femoral component comprising a ball-shaped head having a diameter and a reduced-in-diameter neck extending from said head and having a contact surface; and
   an acetabular cup formed with a socket including a hemispherical surface to pivotally retain said head, said socket defining an opening at least equal to said diameter of said ball shaped head, said socket defining a proximal end and a distal end and being bounded peripherally at said distal end by a rim having a width which engages said contact surface and establishes an initial contact point corresponding to a predetermined motion limit between said femoral component and said cup, the rim consisting of a continuous convex surface extending distally from said socket for the majority of the width of said rim which is shaped relative to said contact surface so that the contact point between said contact surface and said surface of said rim shifts continuously outwardly and distally from said socket along the majority of said surface of the rim as the femoral component moves beyond said predetermined motion limit to thereby reduce the likelihood of dislocation said majority of said convex surface having a center of curvature disposed substantially proximal of said distal end of said socket.

2. A hip replacement kit including:
   a femoral component comprising a ball-shaped head having a diameter and a reduced-in-diameter neck extending from said head and having a contact surface; and an acetabular cup adapted for assembly to said femoral component, said cup formed with a socket including a hemispherical surface to pivotally retain said head, said socket defining an opening at least equal to said diameter of said ball shaped head, said socket defining aproximal end and a distal end and being bounded peripherally at said distal end by a rim having a width which engages said contact surface of said femoral component and establishes an initial contact point corresponding to a predetermined motion limit between said femoral component and said cup, the rim consisting of a continuous convex surface extending distally from said socket for the majority of the width of said rim which is shaped relative to said contact surface so that the contact point between said contact surface and said surface of said rim shifts continuously outwardly and distally from said socket along the majority of said surface of the rim as the femoral component moves beyond said predetermined motion limit to thereby reduce the likelihood of dislocation, said majority of said convex surface having a center of curvature disposed substantially proximal of said distal end of said socket.

* * * * *